US012239628B2

(12) United States Patent
Karelis et al.

(10) Patent No.: US 12,239,628 B2
(45) Date of Patent: Mar. 4, 2025

(54) CANNABIS COMPOSITION

(71) Applicant: ZELIRA THERAPEUTICS OPERATIONS PTY LTD, Perth (AU)

(72) Inventors: Harry Karelis, Perth (AU); Mara Gordon, Bodega Bay, CA (US); Stewart Smith, Bodega Bay, CA (US); Stewart Washer, Stirling (AU)

(73) Assignee: Zelira Therapeutics Operations Pty Ltd, Perth (AU)

( * ) Notice: Subject to any disclaimer, the term of this patent is extended or adjusted under 35 U.S.C. 154(b) by 0 days.

(21) Appl. No.: 18/460,012

(22) Filed: Sep. 1, 2023

(65) Prior Publication Data

US 2023/0414559 A1    Dec. 28, 2023

Related U.S. Application Data

(63) Continuation of application No. 17/865,024, filed on Jul. 14, 2022, now Pat. No. 11,779,562, which is a continuation of application No. 16/322,447, filed as application No. PCT/AU2017/050814 on Aug. 3, 2017, now abandoned.

(60) Provisional application No. 62/370,304, filed on Aug. 3, 2016.

(51) Int. Cl.
| | |
|---|---|
| *A61K 31/352* | (2006.01) |
| *A61K 31/05* | (2006.01) |
| *A61K 47/06* | (2006.01) |
| *A61P 25/20* | (2006.01) |
| *A61K 36/185* | (2006.01) |

(52) U.S. Cl.
CPC ............ *A61K 31/352* (2013.01); *A61K 31/05* (2013.01); *A61K 47/06* (2013.01); *A61P 25/20* (2018.01); *A61K 36/185* (2013.01)

(58) Field of Classification Search
CPC ...... A61K 31/352; A61K 31/05; A61K 47/06; A61K 36/185; A61K 2300/00; A61K 31/015; A61K 31/045; A61P 25/20; A61P 43/00; Y02A 50/30
USPC ......................................................... 514/456
See application file for complete search history.

(56) References Cited

U.S. PATENT DOCUMENTS

| | | | |
|---|---|---|---|
| 11,304,925 | B1 | 4/2022 | Karelis et al. |
| 11,779,562 | B2 | 10/2023 | Karelis et al. |
| 2012/0004251 | A1 | 1/2012 | Whalley |
| 2014/0271940 | A1 | 9/2014 | Wurzer |
| 2015/0313868 | A1 | 11/2015 | Morgan |
| 2015/0374770 | A1 | 12/2015 | Crowley |
| 2016/0106705 | A1 | 4/2016 | Verzura et al. |
| 2016/0151328 | A1 | 6/2016 | Doane et al. |
| 2016/0346339 | A1* | 12/2016 | Finley .................. A61K 36/185 |
| 2022/0202767 | A1 | 6/2022 | Karelis et al. |
| 2022/0218650 | A1 | 7/2022 | Karelis |
| 2023/0218566 | A1 | 7/2023 | Hopkins et al. |
| 2023/0270808 | A1 | 8/2023 | Gordon et al. |
| 2023/0364052 | A1 | 11/2023 | Karelis |
| 2023/0404944 | A1 | 12/2023 | Takechi et al. |

FOREIGN PATENT DOCUMENTS

| | | |
|---|---|---|
| EP | 1802274 | 7/2007 |
| GB | 2400319 | 10/2004 |
| GB | 2478595 | 9/2011 |
| GB | 2496688 | 5/2013 |
| JP | 2005-272388 | 10/2005 |
| JP | 2007-246428 | 9/2007 |
| KR | 20110120153 | 11/2011 |
| WO | 2013045891 | 4/2013 |
| WO | 2013/165251 | 11/2013 |
| WO | 2014/100231 | 6/2014 |
| WO | 2014/145490 A2 | 9/2014 |
| WO | 2015/065544 A1 | 5/2015 |
| WO | 2015/068052 | 5/2015 |
| WO | WO 2015065544 * | 5/2015 |
| WO | 2015/200049 A1 | 12/2015 |
| WO | 2016/030369 A1 | 3/2016 |
| WO | 2016/064987 | 4/2016 |
| WO | 2016/094810 | 6/2016 |
| WO | 2016123475 | 8/2016 |
| WO | 2016138505 | 9/2016 |
| WO | 2018/023164 | 2/2018 |
| WO | 2018/023166 | 2/2018 |

OTHER PUBLICATIONS

Office Action and Search Report issued in respect of Correspondence Peruvian Application No. 003000330-2019/DIN, dated Sep. 13, 2021, together with an English translation.
Office Action and Search Report issued in respect of corresponding Colombian Patent Application No. NC2019/0001044 dated Jun. 18, 2021, 21 pgs.

(Continued)

*Primary Examiner* — Taylor V Oh
(74) *Attorney, Agent, or Firm* — Armstrong Teasdale LLP

(57) ABSTRACT

The present invention relates to a method for treating a sleep disorder. Preferably, the invention relates to a method for treating a sleep disorder comprising the step of administering a pharmaceutical composition comprising a *Cannabis* extract and optionally one or more pharmaceutically acceptable carriers, diluents, adjuvants, excipients or any combination thereof, the *Cannabis* extract comprising a terpene fraction comprising limonene in an amount of at least about 5.4% by weight of the terpene fraction.

15 Claims, No Drawings

(56) References Cited

OTHER PUBLICATIONS

Murillo-Rodriguez, et al., "Potential effects of cannabidiol as a wake-promoting agent". Current Neuropharmacology, 2014, vol. 12, No. 3, pp. 269-272.
Peace, et al., "Analysis of a Commercial Marijuana e-Cigarette Formulation", Journal of Analytical Toxicology 2016, 10, pp. 374-378.
Analytical 360 | Cannabis Analysis Laboratory for Medical Marijuana. Test Results: B604 Marion Berry CO2 Oil, Nov. 30, 2015, 4 pgs.
Analytical 360 | Cannabis Analysis Laboratory for Medical Marijuana. Test Results: Pain Relief Salve (Yin-Yang Botanicals), May 4, 2014, 4 pgs.
Analytical 360 | Cannabis Analysis Laboratory for Medical Marijuana. Test Results: Test Batch 2x ACDC Coco Tab Dil, Mar. 8, 2014, 4 pgs.
OG Kush Cannabis Strain Research and Information, https://web.archive.org/web/20160321022729/https://www.Atikileatcom/strain/og-kush/, Aug. 10, 2021, 4 pgs.
Shannon et al., Effectiveness of cannabidiol oil for pediatric anxiety and insomnia as part of posttraumatic stress disorder a case report, Perm J. 2016, 20(4), 4 pgs.
Third Office Action issued in respect of corresponding New Zealand Patent Application No. 750359 dated Aug. 10, 2021, 8 pgs.
Gurgel Do Vale, et al., "Central effects of citral, myrcene and limonene, constituents of essential oil chemotypes from Lippia alba (Mill.) N.E. Brown", Phytomedicine 9: 709-714, 2002, 6 pgs.
Analytical 360 | Cannabis Analysis Laboratory for Medical Marijuana Patients; ACDC Oil #2; Posted online Jan. 9, 2015; 4 pages <archive.analytical360.com/m/archived/336512>.
Analytical 360 | Cannabis Analysis Laboratory for Medical Marijuana Patients; C02 Ogre CBD Oil; Posted online Dec. 23, 2013; 4 pages <archive.analytical360.com/m/archived/158120>.
Marchini et al., "Multidimensional analysis of cannabis volatile constituents:Identification of 5,5-dimethyl-1-vinylbicyclo[2.1.1]hexane as avolatile marker of hashish, the resin of *Cannabis saliva* L." Journal of Chromatography A, 1370, pp. 200-215 (2014).
"Ogre Kush Cannabis Strain Research and Information" found online May 18, 2021; 3 pages <https://web.archive.org/web/20160519180605/https://www.wikileaf.com/strain/ogre-kushi>.
Russo et al., "Cannabis, Pain, and Sleep: Lessons from Therapeutic Clinical Trials of Sativex®, a Cannabis-Based Medicine," Chemistry & Biodiversity, 4; pp. 1729-1743 (2007).
"ACDC Strain Information—Leafly" 7 pages (2016) <https://web.archive.org/web/20160317191410mpihttps://www.leafly.com/hybrid/acdc>.
First Office Action issued in corresponding South Korean Patent Application No. 10-20217002290 dated Apr. 7, 2021 together with an English translation.
Second Examination Report issued in corresponding New Zealand Patent Application No. 750359 dated Apr. 14, 2021.
Babson et al., "Cannabis, Cannabinoids, and Sleep: a Review of the Literature," Curr. Psychiatry Rep., 19(23), 12 pages (2017).
"Myrcene: An Abundant Terpene With Surprising Benefits," available online at <https://www.royalqueenseeds.com/blog-myrcene-an-abundant-terpene-with-surprising-benefits-n471>; 14 pages (Apr. 21, 2017).
Analytical 360; Cannabis Analysis Laboratory for Medical Marijuana; Test Results: ACDC Test #170, Posted on Apr. 20, 2014 (3 pages).
Analytical 360; Cannabis Analysis Laboratory for Medical Marijuana; Test Results: Ache-less Roll, Posted on Jan. 17, 2016 (3 pages).
Analytical 360; Cannabis Analysis Laboratory for Medical Marijuana; Test Results: Pain Relief Budder, Posted on Nov. 16, 2015 (3 pages).
Russo "Taming THC: potential cannabis synergy and phytocannabinoid-terpenoid entourage effects," Br J Pharmacol., 163(7), pp. 1344-1364 (2011).
Do Vale et al., "Central effects of citral, myrcene and limonene, constituents of essential oil chemotypes from Lippia alba (Mill.) n.e. Brown," Phytomedicine, 9(8), pp. 709-714 (2002).
International Search Report corresponding to PCT/AU2017/050814 mailed Nov. 7, 2017; 5 pages.
Written Opinion of the International Searching Authority corresponding to PCT/AU2017/050814 completed Nov. 7, 2017; 4 pages.
Murillo-Rodriguez et al., 'Cannabidiol, a constituent of *Cannabis sativa*, modulates sleep in rats', FEBS Letters 2006, 580, 4337-4345.
Romano, et al., 'Cannabis oil: Chemical evaluation of an upcoming cannabis-based medicine', Cannabinoids 2013, 7(1), 1-11.

* cited by examiner

CANNABIS COMPOSITION

FIELD

The invention relates to a method for treating a sleep disorder. The invention also relates to a pharmaceutical composition comprising an extract from a *Cannabis* plant, and its use in the treatment of the sleep disorder.

BACKGROUND

The biological activity of *Cannabis* is well known, and has led it to become a "recreational" drug. However, with the discovery of a class of cannabinoid (CB) receptors, and the relaxation of laws regulating *Cannabis* use—in some jurisdictions decriminalisation—there now exists the opportunity to explore the potential of *Cannabis* as a source of new therapeutics.

There is also a growing movement of patients suffering from chronic diseases, such as sleep disorders, to seek natural remedies as alternative or complementary therapy.

Accordingly, there is a continuing need to develop new treatments for sleep disorders, which is derived, at least in part, from a natural source.

SUMMARY

The invention provides a method of treating a sleep disorder comprising administering to a patient in need thereof an effective amount of a pharmaceutical composition comprising a *Cannabis* extract. Accordingly, also provided is a pharmaceutical composition comprising the *Cannabis* extract and optionally one or more pharmaceutically acceptable carriers, diluents, adjuvants, excipients or any combination thereof.

The *Cannabis* extract comprises a cannabinoid fraction and a terpene fraction. The cannabinoid fraction typically comprises as the primary cannabinoid $\Delta^9$-Tetrahydrocannabinol (THC) or Cannabidiol (CBD). The cannabinoid fraction may also comprise one or more further cannabinoids selected from Cannabinol (CBN) and $\Delta^9$-Tetrahydrocannabivarin (THCV). The terpene fraction typically comprises beta-myrcene. The terpene fraction may further comprise one or more of linalool, nerolidol and limonene. When present, the limonene may be present in an amount of at least about 5.4% by weight of the terpene fraction.

In one aspect, there is provided a pharmaceutical composition comprising a *Cannabis* extract and optionally one or more pharmaceutically acceptable carriers, diluents, adjuvants, excipients or any combination thereof, the *Cannabis* extract comprising a terpene fraction comprising limonene in an amount of at least about 5.4% by weight of the terpene fraction.

Preferably, the *Cannabis* extract comprises $\Delta^9$-Tetrahydrocannabinol (THC), Cannabidiol (CBD), Cannabinol (CBN) and beta-myrcene.

In one embodiment of the present invention the THC in the pharmaceutical composition is in an amount from 0% to 90% by weight of the extract.

In some embodiments of the present invention the pharmaceutical composition further comprises one or more of beta-caryophyllene, linalool, nerolidol 1, ocimene, alpha-pinene, and beta-pinene.

In one embodiment of the present invention the THC in the pharmaceutical composition is in an amount from 0% to 90% by weight of the extract.

In some embodiments of the present invention the pharmaceutical composition further comprises one or more of beta-caryophyllene, linalool, nerolidol 1, ocimene, alpha-pinene, and beta-pinene.

In a further aspect, there is provided use of the *Cannabis* extract in the preparation of a medicament for treating a sleep disorder.

In yet another aspect, there is provided a pharmaceutical composition for treating a sleep disorder, wherein the pharmaceutical composition comprises a *Cannabis* extract and optionally one or more pharmaceutically acceptable carriers, diluents, adjuvants, excipients or any combination thereof.

In one embodiment, the present invention provides a pharmaceutical composition comprising a *Cannabis* extract comprising a terpene fraction, wherein said composition comprises:
  (i) $\Delta^9$-Tetrahydrocannabinol (THC) in an amount from 0% to 90% by weight of the *Cannabis* extract;
  (ii) Cannabidiol (CBD) in an amount from 0% to 20% by weight of the *Cannabis* extract;
  (iii) Cannabinol (CBN) in an amount from 0% to 20% by weight of the *Cannabis* extract;
  (iv) beta-myrcene in an amount from 0% to 20% by weight of the *Cannabis* extract; and
  (v) limonene in an amount of at least about 5.4% by weight of the terpene fraction; wherein the pharmaceutical composition optionally comprises one or more pharmaceutically acceptable carriers, diluents, adjuvants, excipients or any combination thereof.

In one embodiment, the present invention provides a pharmaceutical composition for treatment of a sleep disorder comprising a *Cannabis* extract comprising a terpene fraction, wherein said composition comprises:
  (i) $\Delta^9$-Tetrahydrocannabinol (THC) in an amount from 0% to 90% by weight of the *Cannabis* extract;
  (ii) Cannabidiol (CBD) in an amount from 0% to 20% by weight of the *Cannabis* extract;
  (iii) Cannabinol (CBN) in an amount from 0% to 20% by weight of the *Cannabis* extract; and
  (iv) beta-myrcene in an amount from 0% to 20% by weight of the *Cannabis* extract; and
  (v) limonene in an amount of at least about 5.4% by weight of the terpene fraction; wherein the pharmaceutical composition optionally comprises one or more pharmaceutically acceptable carriers, diluents, adjuvants, excipients or any combination thereof.

In a further aspect, there is provided use of the *Cannabis* extract in the preparation of a medicament for treating a sleep disorder.

In yet another aspect, there is provided a pharmaceutical composition for treating a sleep disorder, wherein the pharmaceutical composition comprises a *Cannabis* extract and optionally one or more pharmaceutically acceptable carriers, diluents, adjuvants, excipients or any combination thereof.

In a further aspect the present invention provides An oral pharmaceutical solution comprising a *Cannabis* extract comprising a terpene fraction, wherein said composition comprises:
  (i) $\Delta^9$-Tetrahydrocannabinol (THC) in an amount from 0% to 90% by weight of the *Cannabis* extract;
  (ii) Cannabidiol (CBD) in an amount from 0% to 20% by weight of the *Cannabis* extract;
  (iii) Cannabinol (CBN) in an amount from 0% to 20% by weight of the *Cannabis* extract;
  (iv) beta-myrcene in an amount from 0% to 20% by weight of the *Cannabis* extract; and (v) limonene in an amount of at least about 5.4% by weight of the terpene fraction; wherein the pharmaceutical composition optionally comprises one or more pharmaceutically acceptable carriers, diluents, adjuvants, excipients or any combination thereof.

Preferably, the oral pharmaceutical solution is in sublingual spray form.

DESCRIPTION OF EMBODIMENT(S)

The present invention provides a pharmaceutical composition comprising a *Cannabis* extract and optionally one or more pharmaceutically acceptable carriers, diluents, adjuvants, excipients or any combination thereof.

*Cannabis* plants produce a diverse array of secondary metabolites, including cannabinoids, terpenes and terpenoids, sterols, triglycerides, alkanes, squalenes, tocopherols, carotenoids and alkaloids. The mix of these secondary metabolites varies depending on several factors, including *Cannabis* variety, part of the *Cannabis* plant extracted, method of extraction, processing of the extract, and season.

There are several varieties of *Cannabis* plant, which have been described under two distinct naming conventions. One of these conventions identifies three distinct species of *Cannabis* plant, namely *Cannabis sativa* Linnaeus, *Cannabis indica* LAM., and *Cannabis ruderalis*. Another convention identifies all *Cannabis* plants as belonging to the *Cannabis sativa* L. species, with the various varieties divided amongst several subspecies, including: *Cannabis sativa* ssp. *sativa* and ssp. *indica*. As used herein, the term "*Cannabis*" refers to any and all of these plant varieties.

Extracts of *Cannabis* may be prepared by any means known in the art. The extracts may be formed from any part of the *Cannabis* plant containing cannabinoid, terpene and terpenoid compounds. Extracts may be formed by contacting an extractant with a leaf, seed, trichome, flower, keif, shake, bud, stem or a combination thereof. In some embodiments, the extract is formed from the flowers and shake of a *Cannabis* plant. Any suitable extractant known in the art may be used, including, for example, alcohols (e.g. methanol, ethanol, propanol, butanol, propylene glycol etc.), water, hydrocarbons (e.g. butane, hexane, etc.), oils (e.g. olive oil, vegetable oil, essential oil, etc.), a solvent (e.g. ethyl acetate, polyethylene glycol, etc.) or a supercritical fluid (e.g. liquid $CO_2$). The extractant may be completely or partially removed prior to incorporation of the *Cannabis* extract into the pharmaceutical composition, or it may be included in the pharmaceutical composition as a carrier. The extractant may be removed by heating the extract optionally under reduced pressure. It will be appreciated that some of the more volatile plant metabolites (such as terpenes) may also be removed with the extractant. Accordingly, in some embodiments, removing the extractant may enrich the cannabinoid fraction of the extract. In some embodiments, the extract is filtered to remove particulate material, for example, by passing the extract through filter paper or a fine sieve (e.g. a sieve with pore sizes of 5 m).

In some embodiments, the *Cannabis* extract is formed by applying heat and pressure to the plant material. Typically, in these embodiments, no extractant is required.

In some embodiments, the *Cannabis* extract is a *Cannabis* oil. As used herein, a "*Cannabis* oil" is an extract formed by contacting at least a part of a *Cannabis* plant with an oil. The extracting oil may optionally be removed. Extracting oils may be selected from olive oil, hemp oil, sesame oil, coconut oil, vegetable oil, canola oil, grape seed oil, almond oil, medium-chain triglyceride (MCT) oil, and any other edible oil, or a combination thereof.

The term "cannabinoid" as used herein relates to any cannabinoid that have been isolated from a *Cannabis* plant or synthetically created to have activity involving the endocannabinoid system.

The term "cannabinoid fraction" is used to describe the combination of cannabinoid compounds present in the *Cannabis* extract.

The term "terpenes" or "terpenoids" as used herein refers to a class of hydrocarbon molecules, which often provide a unique smell. Terpenes are derived from units of isoprene, which has the molecular formula $C_5H_8$. The basic molecular formula of terpenes are multiples of the isoprene unit, i.e. $(C_5H_8)_n$, where n is the number of linked isoprene units. Terpenoids are terpene compounds that have been further metabolised in the plant, typically through an oxidative process, and therefore usually contain at least one oxygen atom.

The term "terpene fraction" is used to describe the combination of terpene and terpenoid compounds present in the *Cannabis* extract.

The inventors have observed that the efficacy of a pharmaceutical composition is enhanced when the terpene fraction has a certain profile, i.e. a certain proportion of particular terpenes/terpenoids are present in the extract. It is believed that the increase in efficacy may be synergistic (i.e. non-additive). It is also believed that the presence of specific components in the terpene fraction may enhance the patient's tolerance to cannabinoid therapy.

In some embodiments, the *Cannabis* extract contains high amounts (e.g. greater than 50% by weight) of a main cannabinoid, typically THC. In some embodiments, the *Cannabis* extract may comprise the cannabinoid fraction in an amount of about 50% to about 99.999% by weight, for example, about 55% to about 99.999%, about 60% to about 99.999%, about 70% to about 99.999%, about 80% to about 99.999%, about 90% to about 99.999%, about 90% to about 99.99%, about 90% to about 99.9%, or about 90% to about 99.5% by weight of the *Cannabis* extract. In some embodiments, the *Cannabis* extract comprises about 0.001% to about 50% by weight of non-cannabinoids, for example, about 0.001% to about 20% by weight or about 0.001% to about 10% by weight non-cannabinoids.

In some embodiments, the cannabinoid fraction is present from about 0.001 to about 60% by weight of the pharmaceutical composition, for example, about 5% to about 55% or about 10% to about 50% by weight of the pharmaceutical composition.

In some embodiments, one or more additional compounds (e.g. cannabinoid, terpene or terpenoid compounds) may be added to the *Cannabis* extract. The addition of compounds may be to compensate for natural variations in the relative amounts of certain compounds being expressed in the *Cannabis* plant. The added compounds may be synthetic versions of the desired compounds, they may be purified compounds obtained from other *Cannabis* extracts, or they may be added by blending two or more extracts.

To date, over 100 cannabinoids have been identified in *Cannabis* plants. A comprehensive list of these cannabinoids may be found in Mahmoud A. El Sohly and Waseem Gul, "Constituents of *Cannabis sativa.*" *In Handbook of Cannabis* Roger Pertwee (Ed.) Oxford University Press (2014) (ISBN: 9780199662685). Cannabinoids that have been identified in *Cannabis* plants include: Cannabigerol (E)-CBG-C5, Cannabigerol monomethyl ether (E)-CBGM-C5 A, Cannabigerolic acid A (Z)-CBGA-C5 A, Cannabigerovarin (E)-

CBGV-C3, Cannabigerolic acid A (E)-CBGA-C5 A, Cannabigerolic acid A monomethyl ether (E)CBGAM-C5 A and Cannabigerovarinic acid A (E)-CBGVAC3A); (±)-Cannabichromene CBC-C5, (±)-Cannabichromenic acid A CBCA-C5 A, (±)-Cannabivarichromene, (±)-Cannabichromevarin CBCV-C3, (±)-Cannabichromevarinic acid A CBCVA-C3 A); (−)-Cannabidiol CBD-C5, Cannabidiol momomethyl ether CBDMC5, Cannabidiol-C4 CBD-C4, (−)-Cannabidivarin CBDVC3, Cannabidiorcol CBD-CI, Cannabidiolic acid CBDA-C5, Cannabidivarinic acid CBDVA-C3); Cannabinodiol CBNDC5, Cannabinodivarin CBND-C3); $\Delta^9$-Tetrahydrocannabinol $\Delta^9$-THC-C5, $\Delta^9$-Tetrahydrocannabinol-C4 $\Delta^9$-THCC4, $\Delta^9$-Tetrahydrocannabivarin $\Delta^9$-THCV-C3, $\Delta^9$-Tetrahydrocannabiorcol, $\Delta^9$-THCO-CI, $\Delta^9$-Tetrahydrocannabinolic acid A $\Delta^9$-THCA-C5 A, $\Delta^9$-Tetrahydrocannabinolic acid B, $\Delta^9$-THCA-C5 B, $\Delta^9$-Tetrahydrocannabinolic acid-C4 A and/or B $\Delta^9$-THCA-C4 A and/or B, $\Delta^9$-Tetrahydro-cannabivarinic acid A $\Delta^9$-THCVA-C3 A, $\Delta^9$-Tetrahydrocannabiorcolic acid A and/or B $\Delta^9$-THCOA-CI A and/or B), (−)-$\Delta^8$-trans-(6aR,10aR)-OA-Tetrahydrocannabinol OA-THC-C5, (−)-OA-trans-(6aR,10aR)-Tetrahydrocannabinolic acid A OA-THCA-C5 A, (−)-(6aS, 10aR)-$\Delta^9$-Tetrahydrocannabinol (−)-cis-$\Delta^9$-THC-C5); Cannabinol CBN-C5, Cannabinol-C4 CBN-C4, Cannabivarin CBN-C3, Cannabinol C2 CBN-C2, Cannabiorcol CBN-CI, Cannabinolic acid A CBNA-C5 A, Cannabinol methyl ether CBNM-C5, (−)-(9R,10R)-trans-Cannabitriol (−)-trans-CBT-C5, (+)-(9S,10S)-Cannabitriol (+)-trans-CBT-C5, (±)-(9R,10S/9S,10R)-); Cannabitriol (±)-cis-CBT-C5, (−)-(9R,10R)-trans-10-O-Ethyl-cannabitriol (−)-trans-CBT-OEt-C5, (±)-(9R,10R/9S,10S)-Cannabitriol-C3 (±)-trans-CBT-C3, 8,9-Dihydroxy-A6a(10a)-tetrahydrocannabinol 8,9-Di-OH-CBT-C5, Cannabidiolic acid A cannabitriol ester CBDA-C5 9-OH-CBT-C5 ester, (−)-(6aR,9S,10S,10aR)-9,10-Dihydroxyhexahydrocannabinol, Cannabiripsol, Cannabiripsol-C5, (−)-6a,7,10a-Trihydroxy-$\Delta^9$-tetrahydrocannabinol (−)-Cannabitetrol, 10-Oxo-A6a(10a)tetrahydrocannabinol OTHC); (5aS,6S,9R,9aR)-Cannabielsoin CBE-C5, (5aS,6S,9R,9aR)-C3-Cannabielsoin CBE-C3, (5aS,6S,9R,9aR)-Cannabielsoic acid A CBEA-C5 A, (5aS,6S,9R,9aR)-Cannabielsoic acid B CBEA-C5 B; (5aS,6S,9R,9aR)-C3-Cannabielsoic acid B CBEA-C3 B, Cannabiglendol-C3 OH-iso-HHCV-C3, Dehydrocannabifuran DCBF-C5, Cannabifuran CBF-C5), (−)-$\Delta^7$-trans-(1R,3R,6R)-Isotetrahydrocannabinol, (±)-$\Delta^7$-1,2-cis-(1R,3R,6S/1S,3S,6R)-Isotetrahydrocannabivarin, (−)-$\Delta^7$-trans-(1R,3R,6R)-Isotetrahydrocannabivarin; (±)-(IaS, 3aR,8bR,8cR)-Cannabicyclol CBL-C5, (±)-(1aS,3aR,8bR, 8cR)-Cannabicyclolic acid A CBLA-C5 A, (±)-(IaS,3aR, 8bR,8cR)-Cannabicyclovarin CBLV-C3; Cannabicitran CBTC5; Cannabichromanone CBCN-C5, CannabichromanoneC3 CBCN-C3, and Cannabicoumaronone CBCON-C5.

The *Cannabis* extract may comprise 50-99% by weight of a main cannabinoid. The main cannabinoid may be $\Delta^9$-tetrahydrocannabinol (THC) or cannabidiol (CBD). In some embodiments, the *Cannabis* extract comprises the main cannabinoid in an amount of 55-95% by weight of the cannabinoid fraction. Typically, the *Cannabis* extract further comprises one or more secondary cannabinoids. THC or CBD may also be present in the *Cannabis* extract as a secondary cannabinoid. Typically, each secondary cannabinoid is present in an amount from 0.001% to about 30% by weight of the cannabinoid fraction.

The extract may comprise THC in an amount from 0% to 90% by weight of the extract, for example, from 0.001-90% or 2-85% by weight of the extract. When THC is present as the main cannabinoid, the extract may comprise THC in an amount of 40-90%, 50-90% or 55-85% by weight of the extract. When THC is present as a secondary cannabinoid, the extract may comprise THC in an amount of 0.001-20% by weight of THC as a secondary cannabinoid, for example, from 0.001-15% or 0.005-10% by weight of the extract.

Accordingly, in some embodiments, the *Cannabis* extract comprises 0-20% by weight of cannabidiol (CBD) as a secondary cannabinoid, for example, from 0.001-20% or 0-10% by weight of the extract.

In some embodiments, the *Cannabis* extract comprises 0-20% by weight of Cannabinol (CBN), for example, from 0.001-20% or 0-10% by weight of the extract.

In some embodiments, the *Cannabis* extract comprises 0-50% by weight $\Delta^9$-Tetrahydrocannabivarin (THCV), for example, from 0.001-20% or 0-10% by weight of the extract.

Typically, the *Cannabis* extracts also comprise other cannabinoids in addition to THC and/or CBD. These cannabinoids include $\Delta^9$-Tetrahydrocannabinolic acid (THCA), $\Delta^9$-Tetrahydrocannabivarin (THCV), (−)-Cannabidivarin (CBDV) and Cannabigerol (CBG). Each of these cannabinoids may be present in an amount from 0.001% to 30% by weight of the composition.

In some embodiments, certain cannabinoids may be absent, or present in non-detectable amounts (e.g. less than 0.001% by weight of the analyte). In some embodiments, the *Cannabis* extract may exclude one or more of the following cannabinoids: Cannabidiol (CBD), $\Delta^9$-Tetrahydrocannabivarin (THCV), Cannabidiolic acid (CBDA), Cannabigerolic acid (CBGA), Cannabinol (CBN) and (−)-Cannabidivarin (CBDV).

The *Cannabis* extract comprises non-cannabinoid compounds, which typically includes a terpene fraction, i.e. terpenes and terpenoids. In some embodiments, the *Cannabis* extract comprises a terpene fraction in an amount of less than 50% by weight, for example, less than 45%, 40%, 35%, 30%, 25%, 20%, 15%, 10%, 9%, 8%, 7%, 6%, 5%, 4%, 3%, 2% or 1% by weight of the extract. In some embodiments, the *Cannabis* extract may comprise terpene and terpenoid compounds in an amount of more than 0.001% by weight of the extract, for example, more than 0.001%, 0.005%, 0.01%, 0.05%, 0.1%, 0.5%, or 1% of the total weight of the extract. In some embodiments, the *Cannabis* extract comprises about 0.001% to about 50% by weight of terpene and terpenoid compounds, for example, about 0.001% to about 20% by weight, about 0.001% to about 10% by weight, about 0.001% to about 6% by weight or about 0.001 to about 5% by weight of the composition.

Typically, the terpene fraction in the plant material used to form the extract may have a different terpene/terpenoid profile than the terpene profile of the final extract, both in terms of the amounts of specific compounds in the terpene fraction and the weight of the terpene fraction relative to the other components. For example, a *Cannabis* flower may comprise about 20% by weight cannabinoids and about 3% by weight terpenes. Following extraction and concentration (i.e. removal of the extractant), the amount of cannabinoids may increase to an amount of about 50-90% by weight and the terpene fraction may amount to about 0.1-6% by weight of the *Cannabis* extract. This typical scenario shows that while the cannabinoids are concentrated when the extractant is removed, the relative amount of the terpene fraction is reduced, likely due to the volatility of many of the terpenes/terpenoids present in the terpene fraction. Therefore, the profile of the terpene fraction present in the *Cannabis* extract is significantly different from the profile of the terpene fraction that exists in Nature.

A variety of terpenes and terpenoids have also been identified in *Cannabis* extracts, including monoterpenes, monoterpenoids, sesquiterpenes and sesquiterpenoids. For example, the following terpenes and terpenoids have been identified in *Cannabis* extracts: Alloaromadendrene, allyl hexanoate, benzaldehyde, (Z)-a-cis-bergamotene, (Z)-a-trans-bergamotene, β-bisabolol, epi-a-bisabolol, β-bisabolene, borneol (camphol), cis-y-bisabolene, borneol acetate (bornyl acetate), α-cadinene, camphene, camphor, cis-carveol, caryophyllene (B-caryophyllene), α-humulene (α-caryophyllene), γ-cadinene, Δ-3-carene, caryophyllene oxide, 1,8-cineole, citral A, citral B, cinnameldehyde, α-copaene (aglaiene), γ-curcumene, β-cymene, β-elemene, γ-elemene, ethyl decdienoate, ethyl maltol, ethyl propionate, ethylvanillin, eucalyptol, α-eudesmol, β-eudesmol, γ-eudesmol, eugenol, cis-β-famesene ((Z)-β-farnesene), trans-a-farnesene, trans-β-famesene, trans-γ-bisabolene, fenchone, fenchol (norbornanol, β-fenchol), geraniol, a-guaiene, guaiol, methyl anthranilate, methyl salicylate, 2-methyl-4-heptanone, 3-methyl-4-heptanone, hexyl acetate, ipsdienol, isoamyl acetate, lemenol, limonene, d-limonene (limonene), linolool (linalyl alcohol, β-linolool), α-longipinene, menthol, γ-muurolene, myrcene (β-myrcene), nerolidol, trans-nerolidol, nerol, β-ocimene (cis-ocimene), octyl acetate, α-phellandrene, phytol, α-pinene (2-pinene), β-pinene, pulegone, sabinene, cis-sabinene hydrate (cis-thujanol), β-selinene, α-selinene, γ-terpinene, terpinolene (isoterpine), terpineol (α-terpineol), terpineol-4-ol, α-terpinene (terpilene), α-thujene (origanene), vanillin, viridiflorene (ledene), and α-ylange.

It is believed that the presence of the particular terpenes/terpenoids in the terpene fraction is associated with beneficial effects of the pharmaceutical composition in use.

The terpene fraction typically comprises beta-myrcene. It is believed that beta-myrcene may enhance the bioavailability of the cannabinoids present in the extract and/or may assist in allowing the cannabinoids to pass the blood-brain-barrier. Beta-myrcene may be present in an amount of from 0% to about 40% by weight of the extract. In some embodiments, beta-myrcene is present in an amount of about 0-40% by weight of the terpene fraction, for example, from 0.001% to about 25%, 5.1% to 29% or about 5.5% to about 25% of the terpene fraction.

The terpene fraction may further comprise one or more of linalool, nerolidol and limonene.

When present, the limonene may be present in an amount of at least about 5.4% by weight by weight of the terpene fraction, for example, from about 5.5% to about 50% or about 5.5% to about 20% by weight of the terpene fraction. Limonene is a cyclic monoterpene having the molecular formula $C_{10}H_{16}$. There are a number of different naturally occurring isomers; however, the most common form is the dextrorotatory isomer, namely D-limonene.

Linalool is a terpenoid that is found in many flower and spice plants having the molecular formula $C_{10}H_{13}O$. It is believed that when linalool is present in a *Cannabis* extract, that is may provide a sedative effect. In some embodiments, linalool may be present in an amount of at least 0.05% by weight of the terpene fraction. In some preferred embodiments, linalool is present in an amount of at least 5% by weight of the terpene fraction. In other embodiments, linalool is present in amount of from 0.05% to 25% by weight of the terpene fraction, for example, from 0.1% to 20% by weight of the terpene fraction.

Nerolidol is a sesquiterpenoid having the molecular formula of $C_{15}H_{26}O$. It exists in Nature in two isomeric forms, namely nerolidol 1 and nerolidol 2, which differ in the geometry around a central olefin, i.e. either cis or trans isomers. The extract may comprise nerolidol (i.e. both nerolidol 1 and nerolidol 2) in an amount of at least 0.001% by weight of the terpene fraction, for example, from 0.01% to 20% by weight of the terpene fraction. Typically, nerolidol 1 is present in greater amount relative to nerolidol 2. In some embodiments, nerolidol 1 may be absent (or present in an amount below the limit of detection). In some embodiments, nerolidol 2 may be absent (or present in an amount below the limit of detection). In some embodiments, nerolidol 1 and nerolidol 2 are absent (or present in an amount below the limit of detection). Nerolidol 1 may be present in the extract in an amount of at least about 0.001% by weight of the terpene fraction, for example, from 0.001% to 20% or 0.001 to 15% by weight of the terpene fraction. Nerolidol 2 may be present in the extract in an amount of at least about 0.001% by weight of the terpene fraction, for example, from 0.001% to 20% or 0.001 to 15% by weight of the terpene fraction.

The *Cannabis* extract may also comprise a pinene (e.g. alpha-pinene and/or beta-pinene). Pinene is a bicyclic monoterpene having the molecular formula $C_{10}H_{16}$. Pinene is found in Nature in two isomeric forms: alpha-pinene and beta-pinene. The extract may comprise pinene (i.e. alpha-pinene and beta-pinene) in an amount of at least 5% by weight of the terpene fraction, for example, at least 6%, 7%, 8%, 9% or 10% by weight of the terpene fraction. Typically, beta-pinene is present in an amount greater than the amount of alpha-pinene. However, in some embodiments, alpha-pinene is present in greater amount relative to beta-pinene. The ratio of beta-pinene to alpha-pinene may be about 1:1, about 2:1, about 3:1, about 4:1 or about 5:1. Alpha-pinene may be present in the extract in an amount of at least about 0.001% by weight of the terpene fraction, for example, from 0.001% to 30% or from 0.001 to 20% by weight of the terpene fraction. Beta-pinene may be present in the extract in an amount of at least about 0.001% by weight of the terpene fraction, for example, 0.001% to 80%, 10% to 80%, 20% to 75% or 40% to 75% by weight of the terpene fraction.

The terpene fraction may also comprise beta-caryophyllene. Beta-caryophyllene may be present in an amount of at least 0.001% by weight of the terpene fraction, for example, from 0.001% to 20% or 0.001% to 15% of the terpene fraction.

In some embodiments, the extract further comprises humulene. It is believed that that humulene may enhance the sedative properties of the extract. Humulene is also sometimes called alpha-caryophyllene.

The *Cannabis* extract may also include ocimene. Ocimene may be present in an amount of at least 0.001% by weight of the terpene fraction, for example, from 0.001% to 20% or 0.001% to 5% by weight of the terpene fraction.

In some embodiments, the terpene fraction comprises beta-myrcene, D-limonene, beta-caryophyllene, linalool, nerolidol 1, ocimene, alpha-pinene, and beta-pinene.

In some embodiments, the terpene fraction may be present in the composition in an amount from 0.001% to 6% by weight of the extract and may comprise:
  beta-myrcene in an amount of from 0% to 40% by weight of the terpene fraction;
  beta-caryophyllene in an amount of from 0% to 20% by weight of the terpene fraction;

D-limonene in an amount of from about 5.5% to about 50% by weight of the terpene fraction;

linalool in an amount of from 0% to 20% by weight of the terpene fraction;

beta-pinene in an amount of from 0% to 80% by weight of the terpene fraction;

alpha-pinene in an amount of from 0% to 20% by weight of the terpene fraction;

nerolidol 1 in an amount of from 0% to 20% by weight of the terpene fraction;

nerolidol 2 in an amount of from 0% to 20% by weight of the terpene fraction; and ocimene in an amount of from 0% to 20% by weight of the terpene fraction.

In some embodiments, specific terpenes or terpenoids may be absent, or present in non-detectable amounts (e.g. less than 0.001% by weight of the analyte). In some embodiments, one or more of the following terpenes or terpenoids are absent, or present in non-detectable amounts: alpha-bisabolol, caryophyllene oxide, p-cymene, camphene, alpha-terpinene, gamma-terpinene, delta-s-carene, terpinolene, isopulegol, geraniol, and guaiol.

The cannabinoid fraction and the terpene fraction for two exemplary pharmaceutical compositions are set out in the following Tables 1 and 2. Amounts of cannabinoids are reported as determined by high-performance liquid chromatography (HPLC) and amounts of terpenes are reported as determined by gas chromatography (GO). It will be appreciated that, as the *Cannabis* extract is derived from Nature, the amount of each component may vary in some cases by +/−10%, +/−25% or +/−50%. The ranges of amounts corresponding to each of these limits to account for the potential variation in the composition are also shown in Table 1 and 2.

TABLE 1

THC-rich pharmaceutical composition

| Compound | Amount (wt % of composition) | +/−10% | +/−25% | +/−50% |
| --- | --- | --- | --- | --- |
| THCA | 0.809 | 0.7281-0.8899 | 0.60675-1.01125 | 0.4045-1.2135 |
| THC | 2.638 | 2.3742-2.9018 | 1.9785-3.2975 | 1.319-3.957 |
| THCV | 0.035 | 0.0315-0.0385 | 0.02625-0.04375 | 0.0175-0.0525 |
| CBD | ND | — | — | — |
| CBDA | ND | — | — | — |
| CBG | 0.059 | 0.0531-0.0649 | 0.04425-0.07375 | 0.0295-0.0885 |
| CBGA | 0.077 | 0.0693-0.0847 | 0.05775-0.09625 | 0.0385-0.1155 |
| CBN | 0.037 | 0.0333-0.0407 | 0.02775-0.04625 | 0.0185-0.0555 |
| CBC | 0.048 | 0.0432-0.0528 | 0.036-0.06 | 0.024-0.072 |
| Cannabinoid fraction | 3.655 | 3.2895-4.0205 | 2.74125-4.56875 | 1.8275-5.4825 |
| alpha-bisabolol | ND | — | — | — |
| camphene | BDL | — | — | — |
| delta-s-carene | BDL | — | — | — |
| beta-caryophyllene | 0.003 | 0.0027-0.0033 | 0.00225-0.00375 | 0.0015-0.0045 |
| caryophyllene oxide | BDL | — | — | — |
| p-cymene | BDL | — | — | — |
| geraniol | ND | — | — | — |
| guaiol | ND | — | — | — |
| alpha-humulene | BDL | — | — | — |
| isopulegol | BDL | — | — | — |
| D-limonene | 0.005 | 0.0045-0.0055 | 0.00375-0.00625 | 0.0025-0.0075 |
| linalool | 0.002 | 0.0018-0.0022 | 0.0015-0.0025 | 0.001-0.003 |
| beta-myrcene | 0.002 | 0.0018-0.0022 | 0.0015-0.0025 | 0.001-0.003 |
| nerolidol 1 | 0.001 | 0.0009-0.0011 | 0.00075-0.00125 | 0.0005-0.0015 |
| nerolidol 2 | BDL | — | — | — |
| ocimene | 0.001 | 0.0009-0.0011 | 0.00075-0.00125 | 0.0005-0.0015 |
| alpha-pinene | 0.004 | 0.0036-0.0044 | 0.003-0.005 | 0.002-0.006 |
| beta-pinene | 0.020 | 0.018-0.022 | 0.015-0.025 | 0.01-0.03 |
| alpha-terpinene | BDL | — | — | — |
| gamma-terpinene | ND | — | — | — |
| terpinolene | ND | — | — | — |
| Terpene fraction | 0.038 | 0.0342-0.0418 | 0.0285-0.0475 | 0.019-0.057 |
| Total *Cannabis* extract in pharmaceutical composition | 3.711 | 3.3399-4.0821 | 2.78325-4.63875 | 1.8555-5.5665 |

Notes:

"ND" means not detected;

"BDL" means below detection limit (e.g. less than 0.001 mg/gram)

TABLE 2

CBD-rich pharmaceutical composition

| Compound | Amount (wt % of composition) | +/−10% | +/−25% | +/−50% |
|---|---|---|---|---|
| THCA | 0.035 | 0.0315-0.0385 | 0.02625-0.04375 | 0.0175-0.0525 |
| THC | 0.079 | 0.0711-0.0869 | 0.05925-0.09875 | 0.0395-0.1185 |
| THCV | ND | — | — | — |
| CBD | 1.588 | 1.4292-1.7468 | 1.191-1.985 | 0.794-2.382 |
| CBDA | 0.364 | 0.3276-0.4004 | 0.273-0.455 | 0.182-0.546 |
| CBG | 0.027 | 0.0243-0.0297 | 0.02025-0.03375 | 0.0135-0.0405 |
| CBGA | ND | — | — | — |
| CBN | ND | — | — | — |
| CBC | 0.113 | 0.1017-0.1243 | 0.08475-0.14125 | 0.0565-0.1695 |
| Cannabinoid fraction | 2.093 | 1.8837-2.3023 | 1.56975-2.61625 | 1.0465-3.1395 |
| alpha-bisabolol | ND | — | — | — |
| camphene | BDL | — | — | — |
| delta-s-carene | BDL | — | — | — |
| beta-caryophyllene | 0.002 | 0.0018-0.0022 | 0.0015-0.0025 | 0.001-0.003 |
| caryophyllene oxide | BDL | — | — | — |
| p-cymene | BDL | — | — | — |
| geraniol | ND | — | — | — |
| guaiol | BDL | — | — | — |
| alpha-humulene | BDL | — | — | — |
| isopulegol | BDL | — | — | — |
| D-limonene | 0.005 | 0.0045-0.0055 | 0.00375-0.00625 | 0.0025-0.0075 |
| linalool | 0.001 | 0.0009-0.0011 | 0.00075-0.00125 | 0.0005-0.0015 |
| beta-myrcene | 0.005 | 0.0045-0.0055 | 0.00375-0.00625 | 0.0025-0.0075 |
| nerolidol 1 | ND | — | — | — |
| nerolidol 2 | ND | — | — | — |
| ocimene | 0.001 | 0.0009-0.0011 | 0.00075-0.00125 | 0.0005-0.0015 |
| alpha-pinene | 0.013 | 0.0117-0.0143 | 0.00975-0.01625 | 0.0065-0.0195 |
| beta-pinene | 0.047 | 0.0423-0.0517 | 0.03525-0.05875 | 0.0235-0.0705 |
| alpha-terpinene | ND | — | — | — |
| gamma-terpinene | BDL | — | — | — |
| terpinolene | BDL | — | — | — |
| Terpene fraction | 0.073 | 0.0657-0.0803 | 0.05475-0.09125 | 0.0365-0.1095 |
| Total *Cannabis* extract in pharmaceutical composition | 2.213 | 1.9917-2.4343 | 1.65975-2.76625 | 1.1065-3.3195 |

Notes:
"ND" means not detected;
"BDL" means below detection limit (e.g. less than 0.001 mg/gram)

The pharmaceutical composition may further comprise one or more pharmaceutically acceptable carriers, diluents, adjuvants, excipients or any combination thereof.

The carrier, diluent, adjuvant and/or excipient are "pharmaceutically acceptable" meaning that they are compatible with the other ingredients of the composition and are not deleterious to a subject upon or following administration.

The pharmaceutical compositions may be formulated, for example, by employing conventional solid or liquid vehicles or diluents, as well as pharmaceutical additives of a type appropriate to the mode of desired administration (for example, excipients, binders, preservatives, stabilisers, flavours, etc.) according to techniques such as those well known in the art of pharmaceutical formulation (See, for example, Remington: The Science and Practice of Pharmacy, 21st Ed., 2005, Lippincott Williams & Wilkins). The pharmaceutically acceptable carrier may be any carrier included in the United States Pharmacopeia/National Formulary (USP/NF), the British Pharmacopoeia (BP), the European Pharmacopoeia (EP), or the Japanese Pharmacopoeia (JP). In some embodiments, the carrier, diluent, adjuvant and/or excipient may be non-natural (e.g. synthetically produced).

The pharmaceutical composition includes those suitable for oral, rectal, nasal, topical (including buccal and sublingual), vaginal or parenteral (including intramuscular, subcutaneous and intravenous) administration or in a form suitable for administration by inhalation or insufflation.

The *Cannabis* extract, together with a conventional adjuvant, carrier, excipient or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For preparing pharmaceutical compositions from the *Cannabis* extract described herein, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

Liquid form preparations include solutions, dispersions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The *Cannabis* extract can be suspended in a pharmaceutically acceptable carrier, such as sterile water, sterile organic solvent or a mixture of both.

Other liquid form preparations include those prepared by combining the *Cannabis* extract with one or more naturally derived oils (e.g. an essential oil) or waxes. An "essential oil" is an oil derived by extraction (e.g. steam extraction, or contacting the plant material with an extractant) or pressing, which contains primarily hydrophobic, and generally fragrant, components of the plant material. Suitable naturally derived oils and waxes include Sesame oil, Olive oil, *Arnica* essential oil, Lavender essential oil, Lavender Spike essential oil, Frankincense essential oil, Lemongrass essential oil, Cinnamon Leaf essential oil, Rosemary Cineole essential oil, Rosemary essential oil, Bergamot essential oil, Myrrh essential oil, Sage essential oil, Coconut oil, Bees wax and Hemp oil.

The pharmaceutical compositions may be formulated for parenteral administration (e. g. by injection, for example bolus injection or continuous infusion) and may be presented in unit dose form in ampoules, pre-filled syringes, small volume infusion or in multi-dose containers optionally with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

The solvent or dispersion medium for the injectable solution or dispersion may contain any of the conventional solvent or carrier systems, and may contain, for example, water, ethanol, polyol (for example, glycerol, propylene glycol and liquid polyethylene glycol, and the like), suitable mixtures thereof, and vegetable oils.

Pharmaceutical forms suitable for injectable use may be delivered by any appropriate route including intravenous, intramuscular, intracerebral, intrathecal, epidural injection or infusion.

Sterile injectable solutions are prepared by incorporating the *Cannabis* extract in the required amount in the appropriate carrier with various other ingredients such as those enumerated above, as required, followed by sterilisation. Generally, dispersions are prepared by incorporating the various sterilised active ingredients into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile suspension of the active ingredient plus any additional desired ingredients.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active may be incorporated with excipients and used in the form of ingestible tablets, buccal tablets, troches, capsules, elixirs, suspensions, syrups, wafers, and the like.

The amount of active ingredient in therapeutically useful compositions should be sufficient that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations, including those that allow specific delivery of the active peptide to specific regions of the gut.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well-known suspending agents.

Pharmaceutically acceptable carriers and/or diluents include any and all solvents, dispersion media, coatings, antibacterial and antifungal agents, isotonic and absorption delaying agents and the like.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the active ingredients may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension.

In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas.

The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier may form a gel in the nasal cavity. The powder composition may be presented in unit dose form for example in capsules or cartridges of, e.g. gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the dosage unit forms are dictated by and directly dependent on (a) the unique characteristics of the active material and the particular therapeutic effect to be achieved, and (b) the limitations inherent in the art of compounding such an active material for the treatment of a HCV viral infection in living subjects having a diseased condition in which bodily health is impaired.

Also described herein are compositions absent a carrier where the compositions are in unit dosage form. Accordingly, also provided is a medicament comprising the *Cannabis* extract.

In some embodiments, the pharmaceutical composition further comprises an active agent other than the *Cannabis* extract. Any suitable active agent may be used provided that the activity of the active agent and/or the *Cannabis* extract is not diminished when combined.

Methods of Treatment

In another aspect, also provided is a method for treating a sleep disorder. The method comprising administering to a patient in need thereof an effective amount of the pharmaceutical composition described herein.

The pharmaceutical compositions may be used to treat a sleep disorder. Sleep disorders are described in the International Classification of Sleep Disorders (ICDS). ICDS-3 was published in 2014 and characterises sleep disorders as belonging to one of the following classes: (1) Insomnias; (2) Sleep Related Breathing Disorders; (3) Central Disorders of Hypersomnolence; (3) Circadian Rhythm Sleep-Wake Disorders; (4) Parasomnias; (5) Sleep Related Movement Disorders. Accordingly, the sleep disorders to be treated by the pharmaceutical composition may include any sleep disorders from the classes (1) Insomnias; (2) Sleep Related Breathing Disorders; (3) Central Disorders of Hypersomnolence; (3) Circadian Rhythm Sleep-Wake Disorders; (4) Parasomnias; (5) Sleep Related Movement Disorders. In particular, the pharmaceutical compositions may be effective in the treatment of a sleep disorder selected from: insomnia, narcolepsy, hypersomnia, sleep apnoea, periodic limb movement disorder, restless legs syndrome, nocturnal eating (drinking) syndrome, jet lag, shift work sleep disorder, irregular sleep-wake pattern, confusional arousals, sleepwalking, sleep terrors, sleep talking, nightmares, sleep paralysis, REM sleep behaviour disorder, snoring, sleeping sickness, a sleep disorder associated with another disease or condition, or any other sleep disorder.

By "effective amount" it is meant an amount sufficient that when administered to the patient an amount of the drug is provided to achieve an effect. In the case of a therapeutic method, this effect may be the treatment of the sleep disorder. Therefore, the "effective amount" may be a "therapeutically effective amount". By "therapeutically effective amount" it is meant an amount sufficient that when administered to the patient an amount of drug is provided to treat the disease or a symptom of the disease.

As used herein, the terms "treating", "treatment", "treat" and the like mean affecting a subject, tissue or cell to obtain a desired pharmacological and/or physiological effect. The effect may be prophylactic in terms of completely or partially preventing, or reducing the severity of, a disease or associated symptom, and/or may be therapeutic in terms of a partial or complete cure of a disease. A reference to "treating" a sleep disorder therefore encompasses: (a) assisting the patient to fall asleep; (b) assisting the patient remain asleep once sleep has been achieved; (c) relieving or ameliorating the effects of the sleep disorder, e.g. enhancing wakefulness during non-sleep periods; or (d) preventing the sleep disorder from occurring in a subject predisposed to, or at risk of, the sleep disorder, so that the sleep disorder does not develop or occur in the subject, or develops in a less severe form.

The method may also comprise administering an active agent other than the *Cannabis* extract. This active agent may be administered simultaneously or consecutively with the *Cannabis* extract. By consecutively it is meant that each of the *Cannabis* extract and the other active agent are administered separately and may be at different times. Typically, when the *Cannabis* extract and the other active agent are administered consecutively they are administered within 24 hours, or within 12, 8, 6, 5, 4, 3, 2, or 1 hour(s) of each other. The *Cannabis* extract may be administered before or after the other active agent. Further, the route of administration for the *Cannabis* extract and the other active agent may be the same or different.

In another aspect, also provided is the use of the *Cannabis* extract in the preparation of a medicament for the treatment of the sleep disorder.

Also provided is a kit comprising in separate parts:

(a) an effective amount of the *Cannabis* extract; and (b) a pharmaceutically acceptable carrier, diluent, adjuvant, excipient or a combination thereof.

In some embodiments, the kit further comprises a part comprising (c) an effective amount of an active agent other than the *Cannabis* extract.

In another aspect, there is provided the pharmaceutical composition for treating the sleep disorder. The pharmaceutical composition may be any of the pharmaceutical compositions described above, comprising any above-described combination of components, provided that it comprises the *Cannabis* extract with the specified terpene fraction. The sleep disorder may also be any of those described above.

EXAMPLES

The invention will be further described by way of non-limiting examples. It will be understood to persons skilled in the art of the invention that many modifications may be made without departing from the spirit and scope of the invention.

Example 1—*Cannabis* Extracts

The following *Cannabis* extracts are described:

AZ7—infusion of the Ogre Shock plant.

AZ8—infusion of the ACDC plant.

| Component | AZ7 wt %[3] | AZ8 wt %[3] |
|---|---|---|
| Cannabinoids[1] | | |
| THCA | 0.809 | 0.035 |
| THC | 2.638 | 0.079 |
| THCV | 0.035 | 0.000 |
| CBD | 0.000 | 1.588 |
| CBDA | 0.000 | 0.364 |
| CBG | 0.059 | 0.027 |
| CBGA | 0.077 | 0.000 |
| CBN | 0.037 | 0.000 |
| CBC | 0.048 | 0.113 |
| Terpenes[2] | | |
| alpha-bisabolol | 0.000 | 0.000 |
| camphene | BDL | BDL |
| delta-s-carene | BDL | BDL |
| beta-caryophyllene | 0.003 | 0.002 |
| caryophyllene oxide | BDL | BDL |
| p-cymene | BDL | BDL |
| geraniol | 0.000 | 0.000 |
| guaiol | 0.000 | BDL |
| alpha-humulene | BDL | BDL |
| isopulegol | BDL | BDL |
| D-limonene | 0.005 | 0.005 |
| linalool | 0.002 | 0.001 |
| beta-myrcene | 0.002 | 0.005 |
| nerolidol 1 | 0.001 | 0.000 |
| nerolidol 2 | BDL | 0.000 |
| ocimene | 0.001 | 0.001 |
| alpha-pinene | 0.004 | 0.013 |
| beta-pinene | 0.020 | 0.047 |
| alpha-terpinene | BDL | 0.000 |
| gamma-terpinene | 0.000 | BDL |
| terpinolene | 0.000 | BDL |
| total terpenes | 0.038 | 0.073 |
| total | 3.711 | 2.213 |

Notes:
[1]Cannabinoids were detected using HPLC analysis, an amount reported as 0 wt % indicates that the compound was either not detected, or present in an amount below the detection limit of the HPLC;
[2]Terpenes were detected using GC analysis, an amount reported as 0 wt % indicates that the compound was either not detected, or present in an amount below the detection limit of the GC;
[3]In order to allow for Natural variation, amount within +/−10%, +/−25% or +/−50% of the reported values.

Unless the context requires otherwise, all percentages referred to herein are percentages by weight of the pharmaceutical composition.

The term "about", when used to describe a value, preferably means an amount within ±10% of that value.

The terms "a", "an", "and" and/or "the" and similar referents in the context of describing the invention and the claims which follow are to be construed to cover both the singular and the plural, unless otherwise indicated herein or clearly contradicted by context.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method for treating a sleep disorder, comprising administering to a patient in need thereof an effective amount of a pharmaceutical composition, wherein the pharmaceutical composition comprises a *Cannabis* extract and optionally one or more pharmaceutically acceptable carriers, diluents, adjuvants, excipients or any combination thereof, the *Cannabis* extract comprising:

$\Delta^9$-Tetrahydrocannabinol (THC) in an amount of from 50% to 90% by weight of the *Cannabis* extract;

Cannabidiol (CBD) in an amount of up to 10% by weight of the *Cannabis* extract;

Cannabinol (CBN) in an amount of up to 10% by weight of the *Cannabis* extract; and a terpene fraction in an amount of more than 1% by weight of the *Cannabis* extract, the terpene fraction comprising:

a nerolidol being absent or in an amount of from about 0.01% to about 20% by weight of the terpene fraction;

beta-myrcene in an amount of up to 40% by weight of the terpene fraction;

linalool in an amount of at least 5% by weight of the terpene fraction;

alpha-pinene in an amount of from 0.001% to 20% by weight of the terpene fraction; and beta-pinene in an amount of from 0.001% to 80% by weight of the terpene fraction.

2. The method according to claim 1, wherein the *Cannabis* extract comprises THC in an amount from 55 to 85% by weight of the extract.

3. The method according to claim 1, wherein the *Cannabis* extract comprises $\Delta^9$-Tetrahydrocannabivarin (THCV) in an amount from 0.001% to 10% by weight of the *Cannabis* extract.

4. The method according to claim 1, wherein the terpene fraction comprises beta-pinene in an amount of at least 5% by weight of the terpene fraction.

5. The method according to claim 1, wherein the terpene fraction comprises alpha-pinene in an amount of from about 0.001% to 20% by weight of the terpene fraction.

6. The method according to claim 5, wherein the terpene fraction comprises alpha-pinene in an amount of at least 5% by weight of the terpene fraction.

7. The method according to claim 1, wherein the terpene fraction comprises a nerolidol in an amount of from about 0.01% to about 20% by weight of the terpene fraction.

8. The method according to claim 1, wherein the terpene fraction is present in an amount of up to 10% by weight of the *Cannabis* extract.

9. The method according to claim 1, wherein the *Cannabis* extract comprises:

THC in an amount from 55 to 85% by weight of the *Cannabis* extract;

CBD in an amount from 0.001% to 10% by weight of the *Cannabis* extract;

CBN in an amount from 0.001% to 10% by weight of the *Cannabis* extract;

THCV in an amount from 0.001% to 10% by weight of the *Cannabis* extract;

the terpene fraction is present in an amount of up to 10% by weight of the *Cannabis* extract, and the terpene fraction comprises:

beta-pinene in an amount of at least 5% by weight of the terpene fraction;

alpha-pinene in an amount of from about 0.001% to 20% by weight of the terpene fraction;

beta-myrcene in an amount of up to about 40% by weight of the terpene fraction; and a nerolidol in an amount of from about 0.01% to about 20% by weight of the terpene fraction.

10. The method according to claim 1, wherein the pharmaceutical composition comprises an oil.

11. The method according to claim 1, wherein the composition is administered by a route selected from the group consisting of oral, buccal and sub-lingual.

12. The method according to claim 11, wherein the composition is administered sublingually.

13. The method according to claim 1, wherein the sleep disorder is selected from the group consisting of insomnia, narcolepsy, hypersomnia, sleep apnea, periodic limb movement disorder, restless legs syndrome, nocturnal eating (drinking) syndrome, jet lag, shift work sleep disorder, irregular sleep-wake pattern, confusional arousals, sleepwalking, sleep terrors, sleep talking, nightmares, sleep paralysis, REM sleep behaviour disorder, snoring, or sleeping sickness.

14. The method according to claim 13, wherein the sleep disorder is insomnia.

15. The method according to claim 1, wherein the method achieves one or more of the following:

(a) assisting the patient to fall asleep;

(b) assisting the patient remain asleep once sleep has been achieved; or (c) relieving or ameliorating the effects of the sleep disorder, including enhancing wakefulness during non-sleep periods.

\* \* \* \* \*